United States Patent [19]

Muramoto et al.

[11] 4,173,651

[45] Nov. 6, 1979

[54] METHOD FOR KILLING INSECTS AND/OR FUNGI WITH ELECTRO-MECHANICAL ULTRASONIC NEBULIZER AND COMPOSITION FOR SAID METHOD

[75] Inventors: Takayoshi Muramoto, Hiroshima; Kunitaka Orita, Yanai, both of Japan

[73] Assignee: Fumakilla Limited, Tokyo, Japan

[21] Appl. No.: 696,825

[22] Filed: Jun. 16, 1976

[30] Foreign Application Priority Data

Jun. 23, 1975 [JP] Japan .................................. 50-75706
Jan. 27, 1976 [JP] Japan .................................. 51-7095

[51] Int. Cl.² .......................... A01N 9/24; A01N 9/36; A01N 9/12; A01N 9/20
[52] U.S. Cl. .................................. 424/306; 424/200; 424/210; 424/212; 424/219; 424/300
[58] Field of Search ............... 424/207, 306, 212, 219, 424/200, 210, 300

[56] References Cited

U.S. PATENT DOCUMENTS

| | | | |
|---|---|---|---|
| 2,956,073 | 10/1960 | Whetstone et al. | 424/207 |
| 3,636,059 | 1/1972 | Matsui et al. | 424/306 |
| 3,649,720 | 3/1972 | Leber | 424/212 |
| 3,679,667 | 7/1972 | Fanta | 424/306 |
| 3,709,960 | 1/1973 | Lutz et al. | 424/212 |

OTHER PUBLICATIONS

"Pesticides"—Chem. Week—pp. 44, 51, 59 and 62 (Apr. 12, 1969), Neumeyer et al.
Kirk–Othmer, Encyclopedia of Chem. Technology, 2nd ed., vol. 18, pp. 634, 636, 643, 651 and 652 (1969).

*Primary Examiner*—Douglas W. Robinson
*Attorney, Agent, or Firm*—James E. Nilles

[57] ABSTRACT

A novel method for killing insects and/or fungi comprising vaporizing in air an insecticidal and/or fungicidal agent with an electro-mechanical ultrasonic nebulizer and an insecticidal and/or fungicidal composition to be employed in this method are disclosed.

**14

METHOD FOR KILLING INSECTS AND/OR FUNGI WITH ELECTRO-MECHANICAL ULTRASONIC NEBULIZER AND COMPOSITION FOR SAID METHOD

This invention relates to a novel method for killing insects and/or fungi comprising vaporizing in air an insecticidal and/or fungicidal agent with an electro-mechanical ultrasonic nebulizer as well as to an insecticidal and/or fungicidal composition to be employed in this method.

The conventional methods for killing insects and/or fungi are, first of all, the spraying through an atomizer of an insecticidal and/or fungicidal agent in emulsion, oil suspension, or aqueous solution; secondly, release, by heat, of an insecticidal and/or fungicidal agent in air, as observed in fumigants, mosquito-killing coils or electric mosquito-killing device; and thirdly, the spraying of an aerosol of an insecticidal and/or fungicidal agent by gas pressure. Of these methods, the spraying by atomizer is not capable of realizing a uniform dispersion of an insecticidal and/or fungicidal agent over a wide area. To increase the overall effect of the spraying, a large quantity of the agents is needed. For this reason, this method is not economical. The second conventional method releases only a small quantity of an insecticidal and/or fungicidal agent in a given time, so, a considerably long time of application is needed to do the job. The last method of using an aerosol is generally more expensive than the first two.

Therefore, the principal object of this invention is to provide a novel method for killing insects and/or fungi which has overcome the above mentioned defects of the conventional methods as well as an insecticidal and/or fungicidal composition to be employed in this method. The detailed description of this invention will be carried in the following passages.

This invention relates to a novel method for killing insects and/or fungi characterized by vaporizing in air an insecticidal and/or fungicidal agent atomized with an electromechanical ultrasonic nebulizer, and an insecticidal and/or fungicidal composition to be employed in this method.

The electro-mechanical ultrasonic nebulizer to be employed in the method of this invention is such that the number of vibrations is 500,000–3,000,000 Hz when water is used as solvent, and 300,000–2,000,000 Hz when an organic solvent is used, and the outlet-power may be about 10–40 W. The insecticidal and/or fungicidal agents may be commercial ones; for example, organic phosphorus insecticides such as fenitrothion, ciafos, diazinon, DDVP, etc.; carbamate insecticides such as carbaryl, BPMC, MTMC, etc.; pyrethroid insecticides such as pyrethrin, allethrin, tetramethrin, resmethrin, etc.; organic sulfur fungicidal agents such as zineb, maneb, thiuram, etc.; organic phosphorus fungicidal agents such as IBP, EDDP, etc.; antibiotics such as streptomycin, polyoxin, etc.; and other miscellaneous fungicidal agents such as DPC, dichlone, quinoxaline, anilazine, etc. Of course, other insecticides and/or fungicides may be employed.

A suitable particle size of the above mentioned insecticidal and/or fungicidal agents when they are released into air can be selected by varying the number of vibrations of the ultrasonic nebulizer. The co-relationship between the particle size and the number of the vibrations is illustrated in the following tables.

Table I.

| (on oil base) | |
|---|---|
| Number of Vibrations (MHz) | Average Particle Size ($\mu$) |
| 0.8 | 4.3 |
| 1.0 | 3.7 |
| 1.2 | 3.3 |
| 1.4 | 2.9 |
| 1.6 | 2.6 |
| 1.8 | 2.3 |
| 2.0 | 2.0 |

Table II.

| (on water base) | |
|---|---|
| Number of Vibrations (MHz) | Average Particle Size ($\mu$) |
| 0.8 | 5.4 |
| 1.0 | 4.5 |
| 1.2 | 3.9 |
| 1.4 | 3.5 |
| 1.6 | 3.1 |
| 1.8 | 2.8 |
| 2.0 | 2.6 |

Atomization is also made possible at low temperatures with the nebulizer. If the released particle size is as small as 0.5 to 5 microns, the insecticidal and/or fungicidal agent can be uniformly dispersed with great ease. More than that, since the agent is easily inhaled as poison by noxious insects, it has only to be used in a small quantity to exhibit its effect. In addition, vaporization at low temperatures will eliminate the loss of the active ingredient from the agent. Another advantage of our method is apparent when it is employed in agricultural or horticultural buildings such as greenhouse or vinyl plastic hothouse. Manual labor that accompanies the conventional method of application, for example, by spraying or evaporation, is entirely unnecssary for our insecticidal and/or fungicidal method, and therefore, not only is a saving of labor achieved but the health of workers is ensured. In addition, the temperature and moisture in the insulated agricultural or horticultural buildings are so high that plants in them are easily infested with harmful insects. However, according to the method of our invention, because the agent is atomized and vaporized at high concentrations, its application will not result in the increase of humidity. What is more, uniform dispersion of the agent is possible within a short period, covering the wide space of a greenhouse, for example.

We now describe in detail the insecticidal and/or fungicidal composition to be employed in the electro-mechanical ultrasonic nebulizer of the present invention.

According to the inventors' research, atomization with the nebulizer is influenced by the concentration of the insecticidal and/or fungicidal component and the type of a solvent used. By studying the relationship between the concentration of the active ingredient and the solvent, the inventors have confirmed a phenomenon that would never have been imagined by the conventional prior art, that is, a stable and less expensive insecticidal and/or fungicidal composition can be provided by preferably using water or aliphatic hydrocarbons having a boiling point of 150°–350° C. as solvent for the active ingredient that is to be atomized with the nebulizer according to the method of this invention. It is essential that the aliphatic hydrocarbons that can be used as solvent have a boiling point of 150°–350° C. At temperatures below 150° C., the obtained composition is not commercially acceptable because the active ingredient is not uniformly atomized and too much atomization of the solvent causes varied concentrations of the active ingredient. On the other hand, if the solvent boils over 350° C., the result is not also practical because of less atomization as well as absorption of the energy of ultrasonic waves, which causes heating of the solution and decomposition of the active ingredient.

The aliphatic hydrocarbons having 10–18 carbon atoms satisfy the above requirements. When the carbon number is below ten as in n-octane or nonane, the composition of the released particles differs from that of the solution. In the case of for example n-eicosane of twenty carbon atoms, atomization becomes much harder.

The aliphatic hydrocarbons that may be employed in this invention include n-decane, n-undecane, n-dodecane, n-tridecane, n-tetradecane, n-pentadecane, n-hexadecane, n-heptadecane, n-octadecane and isomers thereof, and kerosene. Solvents other than the aliphatic hydrocarbons, such as aromatic hydrocarbons, halogenated hydrocarbons, alcohols, ketones, esters, and ethers, are impractical since some undergo not only alterations in the concentration of the active ingredient but decomposition of the same, and others will absorb the energy of ultrasonic waves to become refractory to atomization.

The concentration of the insecticidal and/or fungicidal composition mentioned above may not exceed 25% by weight. A concentration greater than this level is not applicable on an industrial scale because too much decomposition of the active ingredient takes place. The effective concentration ranges preferably from 2 to 20% by weight. In contrast with the conventional method of using an oil suspension, our method allows an effective application of a small quantity of the insecticidal and/or fungicidal composition at high concentrations, and therefore, contamination of the active ingredient by the solvent is at minimum and an extremely economical operation of the method is realized. The insecticidal and/or fungicidal composition thus prepared is atomized with an electro-mechanical ultrasonic nebulizer having a frequency within the range of from 300,000 to 2,000,000 Hz.

In this instance, if the solvent is water and the active ingredient of the composition is water soluble, said composition may be prepared as an aqueous dilution, but if it is insoluble, the composition may preferably be emulsified by addition of a surfactant. The surfactant includes anion and nonion surfactants and is exemplified by metal salts of alkyl benzene sulfonic acids, sorbitan higher fatty acid esters and polyoxyethylene alkyl esters.

This invention will be more specifically explained by the following working examples and experimental data.

EXAMPLE 1

A solution of allethrin (20 g) in n-pentadecane (80 g) was atomized and vaporized with a electro-mechanical ultrasonic nebulizer.

EXAMPLE 2

A solution of d-cis, trans-allethrin (10 g) in n-hexadecane (90 g) was atomized and vaporized with a electro-mechanical ultrasonic nebulizer.

EXAMPLE 3

A solution of resmethrin (5 g) in n-hexadecane (95 g) was atomized and vaporized with an electro-mechanical ultrasonic nebulizer.

EXAMPLE 4

A solution of DDVP (5 g) in n-tetradecane (90 g) and isopropyl alcohol (5 g) was atomized and vaporized with an electro-mechanical ultrasonic nebulizer.

EXAMPLE 5

A solution of d-cis, trans-resmethrin (5 g) in n-hexadecane (95 g) was atomized and vaporized with an electromechanical ultrasonic nebulizer.

EXAMPLE 6

D-Cis, trans-allethrin (5 g) and d-cis, transresmethrin (5 g) were dissolved in n-dodecane (90 g). The solution was atomized and vaporized with an electro-mechanical ultrasonic nebulizer.

EXAMPLE 7

A surfactant (10 g) was added to fenitrothion (10 g) for dissolution. In use, the solution was emulsified by addition of water (980 g), and atomized and vaporized with an electro-mechanical ultrasonic nebulizer.

EXAMPLE 8

A surfactant (10 g) was added to ciafos (10 g) for dissolution. In use, the solution was emulsified by addition of water (980 g), and atomized and vaporized with an electro-mechanical ultrasonic nebulizer.

EXAMPLE 9

A surfactant (10 g) was added to diazinon (10 g) for dissolution. In use, the solution was emulsified by addition of water (980 g), and was atomized and vaporized with an electro-mechanical ultrasonic nebulizer.

EXAMPLE 10

A surfactant (10 g) was added to DDVP (10 g) for dissolution. The solution was emulsified by addition of water (980 g) before use, and was atomized and vaporized with an electro-mechanical ultrasonic nebulizer.

EXAMPLE 11

A surfactant (10 g) was added to BPMC (10 g) for dissolution. The solution was emulsified by addition of water (980 g) before use, and was atomized and vaporized with an electro-mechanical ultrasonic nebulizer.

EXAMPLE 12

A surfactant (10 g) was added to carbaryl (10 g) for dissolution. The solution was emulsified by addition of water (980 g) before use, and was atomized and vaporized with an electro-mechanical ultrasonic nebulizer.

EXAMPLE 13

A surfactant (1 g) was added to DPC (1 g) for dissolution. The solution was emulsified by addition of water (980 g) before use, and was atomized and vaporized with an electro-mechanical ultrasonic nebulizer.

EXPERIMENT 1

(Efficacy test)

This experiment was conducted in a room of about twenty mats (a mat is 18 square feet). Dishes each containing 10 cockroaches (periplaneta fulliginosa) (female adult) were placed in the four corners (A, B, C and D) and the center (E) of the room. They were then exposed for three hours to the insecticide compositions of Examples 1 to 6, 0.3% oil suspension of DDVP (solvent: kerosene), and 0.5% oil suspension of diazinon (solvent: kerosene) each atomized with an electro-mechanical ultrasonic nebulizer (power: 20 W) at a frequency of 1,300,000 Hz. The exposed insects were transferred to a thermostatic vessel maintained at 25° C., and then the mortality after 24 hours by each composition was determined.

| Com-position | Total atomized amount (ml) | Atomization time (min.) | Result Mortality (%) | | | | |
|---|---|---|---|---|---|---|---|
| | | | A | B | C | D | E |
| Example 1 | 40 | 20 | 100 | 100 | 100 | 100 | 100 |
| Example 2 | 40 | 20 | 100 | 100 | 100 | 100 | 100 |
| Example 3 | 40 | 20 | 100 | 100 | 100 | 100 | 100 |
| Example 4 | 20 | 10 | 100 | 100 | 100 | 100 | 100 |
| Example 5 | 20 | 10 | 100 | 100 | 100 | 100 | 100 |
| Example 6 | 20 | 10 | 100 | 100 | 100 | 100 | 100 |
| DDVP 0.3% oil suspension | 330 | 165 | 100 | 100 | 100 | 100 | 100 |
| Diazinon 0.5% oil suspension | 440 | 200 | 100 | 100 | 100 | 100 | 100 |

EXPERIMENT 2

The experiment was carried out in a room (of about 20 mats) having a capacity of 80 m$^3$. Dishes each containing 15 cockroaches (*Blattella germanica*) (female adult) were placed in the four corners (A, B, C and D) and the center (E) of the room. The insecticide compositions of Examples 7–12 were atomized for about 15 minutes with an electro-mechanical ultrasonic nebulizer (frequency: 1,700,000 Hz, and power: 20 W). The amount of each of the compositions used was 100 g. After 3 hours of exposure to these atomized compositions, the cockroaches were transferred to a thermostatic chamber maintained at 25° C. And then the mortality after 24 hours by each composition was determined.

| Agent | Result Place Mortality (%) | | | | |
|---|---|---|---|---|---|
| | A | B | C | D | E |
| Fenitrothion | 100 | 100 | 100 | 100 | 100 |
| Ciafos | 100 | 100 | 100 | 100 | 100 |
| Diazinon | 100 | 100 | 100 | 100 | 100 |
| DDVP | 100 | 100 | 100 | 100 | 100 |
| BPMC | 100 | 100 | 100 | 100 | 100 |
| Carbaryl | 100 | 100 | 100 | 100 | 100 |

EXPERIMENT 3

The effectiveness of our fungicidal composition against powdery mildew on roses was tested in a vinyl plastic hothouse having a capacity of 1 m$^3$. Three pots of two-year-old roses were placed in the hothouse, and exposed to the fungicidal composition of Example 13 that had been atomized for about 2 minutes with an electro-mechanical ultrasonic nebulizer (frequency: 1,700,000 Hz, and power: 20 W). The amount of the composition used was 10 g. Atomization was performed 5 times every 10 days. Observation of the test results was made 10 days after the 5th atomization.

| Item tested | Result Test area Treated area | Area not treated |
|---|---|---|
| No. of leaves tested | 135 | 128 |
| No. of diseased leaves | 0 | 25 |
| Percent of diseased leaves | 0 | 196 |
| Crop toxicity | Nil | — |

Note: The number of the leaves is the total leaves of the three plants.

EXPERIMENT 4

D-Cis, trans-allethrin in kerosene having the below indicated concentrations were atomized for 15 minutes with an electro-mechanical ultrasonic nebulizer (frequency: 1,300,000 Hz, and power: 15–20 W). The atomized amount and the concentration of the ingredient after atomization were determined.

| | Result | | | | | | |
|---|---|---|---|---|---|---|---|
| Ingredient concentration when prepared | 1% | 5% | 10% | 20% | 25% | 50% | 90% |
| Amount atomized ($\bar{x}n = 10$) | 37ml. | 35ml. | 33ml. | 35ml. | 30ml. | 20ml. | 2ml. |
| Ingredient concentration after atomization | 1% | 5% | 10% | 20% | 26% | 70% | 75% |

As shown above, any concentration of greater than 25% by weight were not commercially acceptable, because the amount atomized was small and a considerable variation occurred in the concentration after atomization. If the original concentration was as high as 90% by weight, decomposition of the insecticidal component took place, followed by an actual decrease in the purity.

What we claim are:
1. A method for killing insects and fungi on plants or in nearby air comprising the steps of:
  applying thereto an insecticidal or fungicidal effective amount of a composition selected from the group consisting of the following solutions, and wherein each solution contains an agent and a solvent, said agent being about 2 to 20% by weight of said composition:
  a solution of allethrin in n-pentadecane;
  a solution of d-cis, trans-allethrin in n-hexadecane;
  a solution of resmethrin in n-hexadecane;
  a solution of DDVP in n-tetradecane and isopropyl alcohol;
  a solution of d-cis, trans-resmethrin in n-hexadecane;
  a solution of d-cis, trans-allethrin and d-cis, trans-resmethrin in n-dodecane;
  a solution of 0.3% oil suspension of DDVP in kerosene;

and a solution of 0.5% oil suspension of diazinon in kerosene;

wherein said composition is applied by nebulization in an electromechanical ultrasonic transducer operating in a frequency range of between 800,000 and 1,700,000 Hz to effect atomization and vaporization in air of a concentration of said composition, the atomized and vaporized particles of said composition having a particle size in the range of 0.5 to 5 microns.

2. A method according to claim 1 wherein said frequency range is about 1,300,000 Hz.

3. A method according to claim 1 wherein said frequency range is about 1,150,000 Hz.

4. A method for killing insects and fungi on plants or in nearby air comprising the steps of:

applying thereto an insecticidal or fungicidal effective amount of a composition selected from the group consisting of the following solutions, and wherein each solution contains an agent and a solvent of:

a solution of allethrin (20%) in n-pentadecane (80%);

a solution of d-cis, trans-allethrin (10%) in n-hexadecane (90%);

a solution of resmethrin (5%) in n-hexadecane (95%);

a solution of DDVP (5%) in n-tetradecane (90%) and isopropyl alcohol (5%);

a solution of d-cis, trans-resmethrin (5%) in n-hexadecane (95%);

a solution of d-cis, trans-allethrin (5%) and d-cis, transresmethrin (5%) in n-dodecane (90%);

a solution of 0.3% oil suspension of DDVP in kerosene;

and a solution of 0.5% oil suspension of diazinon in kerosene;

wherein said composition is applied by nebulization in an electromechanical ultrasonic transducer operating in a frequency range of between 800,000 and 1,700,000 Hz to effect atomization and vaporization in air of a uniform concentration of said composition, the atomized and vaporized particles of said composition having a particle size in the range of 0.5 to 5 microns.

5. A method according to claim 4 wherein said frequency range is about 1,300,000 Hz.

6. A method according to claim 4 wherein said frequency range is about 1,150,000 Hz.

7. A method for killing insects and fungi on plants or in nearby air comprising the steps of:

applying thereto an insecticidal or fungicidal effective amount of a composition selected from the group consisting of the following solutions, and wherein each solution contains an agent, a surfactant containing anion and nonion surfactants, such as metal salts of alkyl benzene sulfonic acids, sorbitan higher fatty acid esters, and polyoxyethylene alkyl esters, and water as a solvent, said agent being about 2 to 20% by weight of said composition:

a solution of fenitrothion;

a solution of ciafos;

a solution of diazinon;

a solution of DDVP;

a solution of BPMC;

and a solution of carbaryl;

wherein said composition is applied by nebulization in an electromechanical ultrasonic transducer operating in a frequency range of between 800,000 and 1,700,000 Hz to effect atomization and vaporization in air of a uniform concentration of said composition, the atomized and vaporized particles of said composition having a particle size in the range of 0.5 to 5 microns.

8. A method according to claim 7 wherein said frequency range is about 1,700,000 Hz.

9. A method according to claim 7 wherein said frequency range is about 1,150,000 Hz.

10. A method for killing insects and fungi on plants or in nearby air comprising the steps of:

applying thereto an insecticidal or fungicidal effective amount of a composition selected from the group consisting of the following solutions, and wherein each solution contains an agent, a surfactant (1%) containing anion and nonion surfactants, such as metal salts of alkyl benzene sulfonic acids, sorbitan higher fatty acid esters, and polyoxyethylene alkyl esters, and water as a solvent:

a solvent of fenitrothion (1%);

a solution of ciafos (1%);

a solution of diazinon (1%);

a solution of DDVP (1%);

a solution of BPMC (1%);

and a solution of carbaryl (1%);

and wherein said composition is applied by nebulization in an electromechanical ultrasonic transducer operating in a frequency range of between 800,000 and 1,700,000 Hz to effect atomization and vaporization in air of a uniform concentration of said composition, the atomized and vaporized particles of said composition having a particle size in the range of 0.5 to 5 microns.

11. A method according to claim 10 wherein said frequency range is about 1,700,000 Hz.

12. A method according to claim 10 wherein said frequency range is about 1,150,000 Hz.

13. A method for killing insects and fungi on plants or in nearby air comprising the steps of:

applying thereto an insecticidal or fungicidal effective amount of a composition consisting of the solution consisting of 1% DPC as an agent, a surfactant and water as a solvent;

wherein said composition is applied by nebulization in an electromechanical ultrasonic transducer operating at a frequency of about 1,700,000 Hz to effect atomization and vaporization in air of a uniform concentration of said composition, the atomized and vaporized particles of said composition having a particle size in the range of 0.5 to 5 microns.

14. A method for killing insects and fungi on plants or in nearby air comprising the steps of:

applying thereto an insecticidal or fungicidal effective amount of a composition consisting of the solution consisting of d-cis, trans-allethrin as an agent, said agent being less than about 25% by weight of said composition, and kerosene as a solvent;

wherein said composition is applied by nebulization in an electromechanical ultrasonic transducer operating at a frequency of about 1,300,000 Hz to effect atomization and vaporization in air of a uniform concentration of said composition, the atomized and vaporized particles of said composition having a particle size in the range of 0.5 to 5 microns.

* * * * *